United States Patent [19]

Sanderson et al.

[11] 4,451,668
[45] May 29, 1984

[54] ALKANE ACETATES PRODUCED BY OXIDATIVE ESTERIFICATION OF OLEFINS OVER TRANSITION METAL BORATES IN THE PRESENCE OF ACETIC ANHYDRIDE

[75] Inventors: John R. Sanderson; Lewis W. Watts, Jr., both of Austin, Tex.

[73] Assignee: Texaco Inc., White Plains, N.Y.

[21] Appl. No.: 402,664

[22] Filed: Jul. 28, 1982

[51] Int. Cl.$^3$ ............................................. C07C 67/05
[52] U.S. Cl. .................................................. 560/246
[58] Field of Search ............... 560/241, 243, 244, 245, 560/246, 247

[56] References Cited

U.S. PATENT DOCUMENTS 3,981,908  9/1976  Ganzler ............................... 560/246
4,220,800  9/1980  Stapp .................................. 560/246

*Primary Examiner*—Michael L. Shippen
*Attorney, Agent, or Firm*—Robert A. Kulason; Jack H. Park; David L. Mossman

[57] ABSTRACT

A process for the production of alkane acetates from olefins in the presence of transition metal borate catalysts, oxygen and acetic anhydride or acetic acid and acetic anhydride via oxidative esterification is described. The reaction is conducted at a temperature in the range of 80° to 280° C. and a pressure of 1 atmosphere or greater. Alkane diacetates and hydroxy acetates are produced which may be used as precursors to alkylene oxides, alkylene glycols and other useful compounds.

17 Claims, No Drawings

ALKANE ACETATES PRODUCED BY OXIDATIVE ESTERIFICATION OF OLEFINS OVER TRANSITION METAL BORATES IN THE PRESENCE OF ACETIC ANHYDRIDE

BACKGROUND OF THE INVENTION

1. Field of the Invention

The invention is related to a process for the production of alkane acetates by the oxidative esterification of olefins, and is particularly related to such a process conducted in the presence of acetic anhydride and/or acetic acid and a transition metal borate catalyst.

2. Description of Relevant Methods

The production of ethylene oxide from ethylene has long been known. However, there has been a less successful search for a similar process for producing propylene oxide directly from propylene in an economic manner. The same processes which produced ethylene oxide cannot be adapted to the production of propylene oxide.

As a result, a number of different schemes to produce propylene oxide from propylene or to produce an intermediate to propylene oxide from propylene have been proposed. Initially the research effort seemed to be directed to producing an olefin oxide directly from the olefin in the presence or absence of a solvent. U.S. Pat. No. 2,649,463 describes the production of a coordination complex created by the reaction of an olefin with a metal halide where the metal is copper, platinum, palladium, iridium, aluminum, zinc, silver, mercury or antimony. This coordination complex is further reacted with oxygen at a high temperature to produce the olefin oxide plus oxygen-containing metal halides. Hawkins, et al. in an article entitled, "Autoxidation of Olefins," in the *Journal of Applied Chemistry,* Vol. 6, 1956, pgs 1 through 10, describes a process for the production of epoxides directly from olefins and molecular oxygen over magnesium oxide and/or cobalt naphthenate. The direct production of olefin oxides from a mono olefin and a saturated hydrocarbon with oxygen and water, organic acids or olefin oxide in low concentration is described in U.S. Pat. No. 2,780,634.

British Patent No. 1,582,261 describes how propylene may be reacted with oxygen over a dinitrogen tetraoxide catalyst in a liquid medium of a chlorinated organic solvent to produce propylene oxide directly. Propylene oxide may also be prepared directly from propylene and oxygen over a catalyst system comprising a palladium cation plus a chloride anion in the presence of a phosphorous or arsenic ligand as revealed in U.S. Pat. No. 4,256,649.

Further, U.S. Pat. No. 2,784,202 outlines how propylene in a liquid hydrocarbon solvent, such as benzene, in the presence of oxygen and water, organic acids or propylene oxide in low concentration yield propylene oxide when heated at a temperature between 130° and 300° C. Propylene oxide is also proposed to be made directly from propylene in benzene in the presence of oxygen over a cobalt, copper, magnesium, vanadium or chromium catalyst where barium or lead is used as a promoter for the catalyst, according to U.S. Pat. No. 3,071,601. Brill, et al. in *Journal of Organic Chemistry,* Vol. 29, 1964, pgs 140–143, describes a process for passing olefins and oxygen, frequently in contact with or dissolved in benzene over various catalysts such as azobisisobutyronitrile, cadmium oxide, cobaltic acetylacetonate, magnesium oxide or methyl ethyl ketone peroxide to produce various oxidation products, including the desired epoxides. U.S. Pat. No. 3,132,156 reveals that ethylene, propylene or butylene oxide may be produced directly from ethane, propane or butane under very precise conditions. These conditions include a temperature of between 425° to 575° C., an oxygen volume percent of between 4 and 14, a contact time with the oxygen of between 0.07–1.5 seconds, a pressure of between 20 to 150 psig and constant concentrations of reactants. Epoxides may also be produced from olefins and oxygen which are in an inert reaction medium when they are brought in contact with a rhenium catalyst and 0.05 to 15 weight percent of a reaction modifier comprised of an alkyl aryl or cyclo alkyl cyanide, pyridine or quinoline in accordance with the invention described in U.S. Pat. No. 3,316,279.

Other schemes for producing olefin oxides from olefins and oxygen by means of a solvent or liquid reaction medium include the following. U.S. Pat. No. 3,153,058 employs polyacyl esters of polyhydroxy alkanes, polyhydroxy cycloalkanes, polyglycols or mixtures thereof as the solvent. Materials selected from saturated aliphatic, alicyclic and aromatic nitriles and mixtures thereof form the solvent in U.S. Pat. No. 3,210,380. Boric acid esters form the liquid reaction medium in U.S. Pat. No. 3,210,381. U.S. Pat. No. 3,228,967 uses major amounts of acetone as the solvent. Carbonic acid esters are employed in U.S. Pat. No. 3,228,968, and at least 25 percent by weight of certain ketones serves as the reaction medium in U.S. Pat. No. 3,232,957. Halogenated benzenes serve as the solvent in U.S. Pat. No. 3,238,229 while benzoic acid esters are employed in a similar reaction described in U.S. Pat. No. 3,281,433. Olefin oxides may be prepared directly from olefins and oxygen over a hydrocarbon soluble, phosphorous molybdenum-hydroxy compound catalyst according to the disclosure in U.S. Pat. No. 3,856,826. The approach of making epoxides directly has never been commercially feasible because all of the methods explored gave low yields of epoxides.

At this point in the history of this research, the emphasis seems to shift from making the olefin oxides directly to making an intermediate which could be converted to the olefin oxides by a second step. For example, U.S. Pat. No. 2,497,408 suggests the production of propylene glycol diacetate from propylene, oxygen and acetic acid over a metal acetate catalyst in which the metal is lead or iron in combination with an alkali earth metal acetate. Another example of this latter approach is U.S. Pat. No. 3,403,175 where olefins in oxygen are reacted in the presence of a reaction medium consisting of carboxylic acid and anhydrides with no catalyst to produce glycol diesters. Acyloxy compounds, which are intermediates to olefin epoxides, may be produced by the reaction of olefins with the metal salt of a carboxylic acid in an aqueous solution if electric current is passed through the solution, according to the method of U.S. Pat. No. 3,453,189. U.S. Pat. No. 3,479,395 reveals that olefins in oxygen may be converted to glycols and glycol acetates by being brought into contact with a solution comprising tellurium dioxide, an alkali metal halide and a redox agent dissolved in a solvent of certain specifications (water, acetic acid, dioxane, dialkyl formamides or dialkyl sulfoxides).

Further examples of the approach to making intermediates to the epoxides include U.S. Pat. No. 3,542,857 where vicinal glycol monoesters and diesters may be made by passing olefins in oxygen in an alkanoic acid medium over cerium salts. A method for making glycol esters from olefins and oxygen in a carboxylic acid medium over tellurium and an appropriate form of bromine is revealed in U.S. Pat. No. 3,668,239. British Patent No. 1,278,353 teaches that nonvicinal glycols may be reacted with carbon monoxide over a rhodium or iridium catalyst together with a halogen promoter to produce dicarboxylic acids which are precursors to diesters which are intermediates to the epoxides. Further, British Patent No. 1,326,219 discloses that glycol esters may be produced from olefins and oxygen in the presence of at least one carboxylic acid when a halogen is employed as an anion and a metal cation is present which is selected from the group of tellurium, cerium, antimony, manganese, arsenic or cobalt. Other examples which reveal how esters may be made from olefins include U.S. Pat. No. 3,770,813 where an olefin with a chloro, hydroxy or lower alkanoyloxy substituent together with oxygen and a monobasic carboxylic acid may be reacted together over an iodide anion and a heavy metal cation of atomic numbers 21 to 30 and 48, and nitrogen-containing cations to give glycol esters. Olefins and oxygen may be reacted together over a catalyst system comprising a metal cation of tellurium, cerium, antimony, vanadium, gallium, arsenic, copper, selenium or silver with a bromine or chlorine anion to produce vicinal glycol esters which are later fractionated to give a residue with a boiling point higher than the vicinal glycol esters according to the disclosure in U.S. Pat. No. 3,789,065. The residue is then contacted with a carboxylic acid to yield additional vicinal glycol esters. British Patent No. 1,353,814 describes the reaction of olefins and oxygen in a carboxylic acid in the liquid phase that contains at least 0.5 percent water over a catalyst system identical to that of the patent previously described to also yield vicinal glycol esters. Ethylene or propylene may be reacted with oxygen in a carboxylic acid over a catalyst system comprising a tellurium cation and a bromide anion or a selenium cation plus a chloride or bromide anion to produce vicinal glycol esters as revealed in U.S. Pat. No. 3,907,874.

Aliphatic hydrocarbon carboxylic acid esters of vicinal glycols which contain organic halogen impurities may be purified by passing them over aquobasic alkali metal compounds, aquobasic earth metal compounds or compounds (other than halides) of zinc, lead, cadmium, tin, mercury, silver, manganese, copper, nickel, cobalt, iron or chromium in accordance with the invention in British Patent No. 1,410,834. German Auslegeschrift No. 2,430,022 describes a multi-step procedure for producing butane diols, which are precursors to butane oxide, from propylene, oxygen and acetic acid.

A system which has obtained a fair amount of commercial importance is described in U.S. Pat. No. 4,045,477 by which vicinal hydroxy esters and diesters are produced from olefins and oxygen over tellurium and an iodide source. Organic monoesters of vicinal glycols may also be produced from olefins, oxygen, water and a carboxylic acid over a system comprising an iodine compound (such as copper iodide, manganese iodide or cerium iodide), a copper compound, and an activated ion taken from the group of manganese, cerium, alkali metals, alkali earth metals, nitric compounds or mixtures thereof, according to the invention in U.S. Pat. No. 4,061,868. U.S. Pat. No. 4,069,381 reveals how glycol monoesters may be made from olefins, oxygen and carboxylic acids over a catalyst system where the cation is zirconium, niobium molybdenum, hafnium, tantalum, tungsten or rhenium where the anion is a halide in the presence of lithium, sodium, potassium, titanium, vanadium, chromium, manganese, iron, cobalt, nickel, copper, zinc, aluminum or silver.

Some of the more recent patents in this field include the following. Esters may be produced from olefins in an acid plus oxygen over a tin or cerium catalyst in the presence of iodide as revealed by U.S. Pat. No. 4,154,957. Saturated vicinal esters may be produced from olefins, carboxylic acids and oxygen in the presence of a boron-containing catalyst according to the invention of U.S. Pat. No. 4,220,800. U.S. Pat. No. 4,221,916 teaches that olefins, carboxylic acids and oxygen when reacted together over a vanadium or ruthenium-containing catalyst can also produce saturated vicinal esters. U.S. Pat. No. 4,238,624 discloses a procedure by which ethylene, oxygen and a lower alkanoic acid are reacted together over an iodine source in a bismuth stabilized tellurium oxide catalyst on a carbon support to give ethylene glycol mono-and dialkanoates.

Further, alkylene glycol dicarboxalates may be made from carboxylic acid esters of monohydric or polyhydric short chain alcohols and olefins and oxygen over a catalyst system comprising tellurium, cerium, antimony, manganese, vanadium, gallium, arsenic or cobalt, plus a halogen anion and a hydrolyzing agent in addition to water as taught by U.S. Pat. No. 4,239,911.

Methods also exist for converting the ester intermediates into the epoxides. For example, U.S. Pat. No. 4,012,423 describes how vicinal hydroxy esters may be reacted over group I, II and IIIA basic metal carboxylates, being the preferred catalyst (sodium, potassium, lithium, calcium or barium, etc.), or group I, II and IIIA basic metal simple oxides and complex oxides and organic bases (such as borates, phosphates, oxides and carboxylates, particularly sodium borate, nickel oxide, etc.) to give epoxides. Another method is described in U.S. Pat. No. 4,158,008 whereby propylene glycol monoesters in the presence of a high boiling solvent is reacted over a base to produce propylene oxide. Propylene oxide may also be produced from propylene glycol with the removal of a water molecule over a weakly acidic carrier comprising a basic alkali metal salt of a low molecular weight carboxylic acid as taught by U.S. Pat. No. 4,226,780.

Of the numerous patents discussed so far, the ones considered to be most relevant to the invention at issue are U.S. Pat. Nos. 4,012,423; 4,069,381 and 4,220,800, all of which have been discussed.

Despite all of the investigative routes described so far and the ones that have been devised which have not been described, there is still a need for an efficient method for making propylene oxide from propylene, in addition to making the alkylene oxides from other olefins, which does not involve a highly corrosive or highly expensive catalyst system.

SUMMARY OF THE INVENTION

The invention concerns a process for the production of alkane acetates comprising reacting an olefin or a mixture of olefins with oxygen and acetic anhydride, in the presence of a transition metal borate catalyst.

DETAILED DESCRIPTION OF THE PREFERRED EMBODIMENTS

Alkane hydroxy acetates and diacetates, also called glycol monoesters or diesters or vicinal diesters, may be prepared by the oxygen or air oxidation of olefins in a carboxylic acid and/or anhydride solvent in the presence of a transition metal borate catalyst. The diacetates may be converted to epoxides or glycols using methods known in the art, some of which have been outlined previously. Both the epoxides and the glycols are of interest in the manufacture of important high volume products, including urethane polyols, gasoline additives, and heat transfer fluids.

According to the method of this invention, the olefin feedstocks may consist of any mono olefin having the double bond located anywhere within the molecule and mixtures of such olefins. The olefin may be an alpha or an internal olefin. Specific examples of suitable feedstocks include, but are not limited by, the following list: propylene, 1-butene, 2-butene, 1-pentene, 2-pentene, 1-hexene, 2-hexene, 3-hexene, heptenes, octenes, nonenes, decenes, undecenes, dodecenes, tridecenes such as 6-tridecene, tetradecenes such as 7-tetradecene, pentadecenes, hexadecenes, etc., and mixtures thereof. Preferably, the olefin has 3 to 16 carbon atoms.

Of course, molecular oxygen in a pure form or air is an essential co-reactant for the method of this invention.

The co-reactant and solvent must be a compound capable of generating a carboxylate ion when it serves as a solvent. These compounds may be generally described as carboxylic acids or anhydrides. They may include materials such as acetic acid, acetic anhydride, carboxylic acids, etc., although acetic acid and acetic anhydride are the preferred solvents/co-reactants. Acetic anhydride may be used alone or in conjunction with acetic acid. It is especially preferred that both acetic anhydride and acetic acid be used together.

Catalysts found to be useful in the method of this invention include transition metal borates. Borate compounds are believed to be novel for the catalysis of olefins to olefin acetates and diacetates (also called esters and diesters) never having been previously discovered. Transition metals are defined as those of Groups IIIB, IVB, VB, VIB, VIIB, VIII, IB and IIB of the Periodic Table. Preferred borates include borates of Group VIII transition metals. Especially preferred borates include nickel borate, copper borate and iron borate. These catalysts are much less corrosive than many of those used in other methods, especially the halide systems. Also, much smaller catalyst levels may be used. They are also less expensive than many of the catalyst systems proposed.

The reaction conditions under which the method of this invention may be conducted include a temperature range of from 80° to 280° C. A preferred range is from 80° to 180° C. The pressure may be one atmosphere or higher. These conditions are much milder than many of those in the prior art discussed earlier.

The invention will be further illustrated by the following examples which are not intended to limit the scope of the invention except as noted.

EXAMPLES 1–20

A resin flask fitted with a condenser, mechanical stirrer, a fritted glass addition tube and thermometer were charged with the reactants and catalyst as shown in Table I. The reaction mixture was then heated to the desired temperature and air bubbled through the reaction mixture for the required length of time. The temperature was maintained at the desired temperature by means of a Therm-0-Watch ® temperature regulator. At the end of the reaction, the mixture was poured into an equal volume of water and shaken until all of the anhydride had hydrolyzed. The organic layer was washed twice more with water and dried over anhydrous sodium sulfate. The total ester was determined by infrared analysis. Other products were determined by nuclear magnetic resonance (NMR).

Examples 1–3 were performed using orthoboric acid, one of the catalysts of U.S. Pat. No. 4,220,800, for comparison with Examples 4–20 using the catalysts of this invention. It may be seen that the yield to ester is much higher using the catalysts of this invention as opposed to those of Examples 1–3 even with lower catalyst concentrations. Within the group of catalysts of this invention, Table I reveals that nickel borate gives a greater yield to total ester (Examples 4–8 and 18–20, 13–77%) than do copper or iron borate (6–50%). Nickel borate is thus the catalyst of preference.

TABLE I

| | OXIDATIVE ESTERIFICATION OF INTERNAL OLEFINS USING TRANSITION METAL BORATE CATALYSTS | | | | | | | | | | | | |
|---|---|---|---|---|---|---|---|---|---|---|---|---|---|
| | Olefin | | Catalyst | | Acetic Anhydride, | Acetic Acid, | Time, | Temperature | Flow Rate, | Total Ester by IR, | Products by NMR, wt. % | | |
| Ex. | ID | ml | ID | g | ml | ml | Hr | °C. | ml/min | % | Olefin | Epoxide | Mono-Acetate | Di-Acetate |
| 1 | 7-Tetradecene | 20.0 | $H_3BO_3$ | 0.53 | 40.0 | — | 15 | 80 | 60–70 | Trace | — | — | — | — |
| 2 | " | 20.0 | $H_3BO_3$ | 1.06 | 40.0 | — | 15 | 90 | 50–60 | 1.7 | — | — | — | — |
| 3 | " | 25.0 | $H_3BO_3$ | 0.53 | 40.0 | — | 18 | 100 | 60 | 3.4 | — | — | — | — |
| 4 | " | 25.0 | $Ni(BO_2)_2$ | 0.216 | 45.0 | — | 18 | 100 | 60 | 64 | 31 | 7 | — | 29 |
| 5 | " | 25.0 | $Ni(BO_2)_2$ | 0.043 | 50.0 | — | 19.5 | 100 | 50 | 75 | — | 19 | — | 36 |
| 6 | " | 25.0 | $Ni(BO_2)_2$ | 0.127 | 50.0 | — | 19.5 | 100 | 50 | 77 | — | 14 | — | — |
| 7 | " | 30.0 | $Ni(BO_2)_2$ | 0.077 | 30.0 | 50.0 | 15.5 | 80 | 45 | 13 | — | — | — | — |
| 8 | " | 30.0 | $Ni(BO_2)_2$ | 0.089 | 30.0 | 50.0 | 15.5 | 90 | 45 | 32 | 58 | 7 | 7 | 9 |
| 9 | " | 25.0 | $Cu(BO_2)_2$ | 0.053 | 30.0 | 50.0 | 6 | 100 | 40–45 | 15 | — | — | — | — |
| 10 | " | 25.0 | $Cu(BO_2)_2$ | 0.112 | 30.0 | 50.0 | 6 | 100 | 40–45 | 10 | 80 | 7 | — | 5 |
| 11 | " | 25.0 | $Cu(BO_2)_2$ | 0.107 | 30.0 | 50.0 | 9 | 90 | 40–45 | 6 | — | — | — | — |
| 12 | " | 25.0 | $Cu(BO_2)_2$ | 0.063 | 30.0 | 50.0 | 9 | 100 | 40–45 | 15 | — | — | — | — |
| 13 | " | 25.0 | $Cu(BO_2)_2$ | 0.067 | 100 | — | 10 | 110 | 40–45 | 50 | — | — | — | — |
| 14 | " | 25.0 | $Cu(BO_2)_2$ | 0.057 | 100 | — | 7 | 110 | 40–45 | 30 | — | — | — | — |
| 15 | " | 20.0 | $Fe(BO_2)_3$ | 0.031 | 50.0 | — | 15.3 | 100 | 50–60 | 43 | — | — | — | — |
| 16 | " | 35.0 | $Cu(BO_2)_2$ | 0.062 | 50.0 | 50.0 | 14.5 | 100 | 40–45 | 31 | 55 | 11 | 3 | 22 |
| 17 | " | 30.0 | $Fe(BO_2)_3$ | 0.029 | 100 | — | 9 | 110 | 40–45 | 41 | — | — | — | — |
| 18 | Undecene/Dodecene | 40.0 | $Ni(BO_2)_2$ | 0.057 | 100 | — | 8.5 | 110 | | 28 | — | — | — | — |
| 19 | Pentadecene/ | 20.0 | $Ni(BO_2)_2$ | 0.030 | 40.0 | — | 14 | 100 | 60 | 32 | 17 | 25 | — | 20 |

TABLE I-continued
OXIDATIVE ESTERIFICATION OF INTERNAL OLEFINS USING TRANSITION METAL BORATE CATALYSTS

| Ex. | Olefin ID | Catalyst ml | Catalyst ID | g | Acetic Anhydride, ml | Acetic Acid, ml | Time, Hr | Temperature °C. | Flow Rate, ml/min | Total Ester by IR, % | Products by NMR, wt. % Olefin | Epoxide | Monoacetate | Diacetate |
|---|---|---|---|---|---|---|---|---|---|---|---|---|---|---|
| 20 | Hexadecene 6-Tridecene | 20.0 | Ni(BO$_2$)$_2$ | 0.022 | 40.0 | — | 14 | 100 | 40–45 | 54 | — | — | — | — |

EXAMPLE 21

This is another comparative example. The procedure used is the same as that disclosed in U.S. Pat. 4,220,800, incorporated by reference herein.

A 1-liter glass-lined reactor equipped with Magnedrive was charged with 150 ml of acetic acid and 150 ml of acetic anhydride, along with 3.60 g of boric acid. Propylene (42 g, 1.12 mol.) was charged and the reactor pressured to 100 psig with oxygen. The reactor was then heated to 140° C. and the reaction continued for 2.5 hours. The pressure was maintained at 350–375 psig by pressuring with oxygen from time to time. The temperature was then raised to 160° C. and continued for 7 hours. The pressure was maintained at 400–420 psig by addition of oxygen from time to time. The reactor was cooled and slowly vented. The acetic acid and acetic anhydride were distilled off at atmospheric pressure. The residue was analyzed by VPC and NMR and found to contain a 26% yield of diacetate with a small amount of monoacetate. Example IV in U.S. Pat. No. 4,220,800 gave a 24.2% yield of diacetate and 2.2% yield of hydroxyacetate.

EXAMPLE 22

The reactor described in Example 21 was charged with 150 ml acetic acid, 150 ml acetic anhydride and 0.145 g of nickel (II) borate. Propylene (42 g, 1.0 ml.) was charged and the reactor heated to 140° C. Oxygen was added slowly to a pressure of 350–375 psig. The reaction was continued for 6 hours and the pressure maintained at 350–375 psig by addition of oxygen from time to time. The reactor was cooled to room temperature, vented and the acetic acid and acetic anhydride distilled off at atmospheric pressure. The residue was weighed and analyzed by NMR. A 24.0% yield of diacetate was obtained. In addition, an 8.8% yield of ethylene diacetate and a 14.2% yield of methylene diacetate was obtained. Although this reaction was conducted 20° C. lower (with a shorter reaction time) than the reaction with boric acid, the yield of diacetate was essentially the same (within experimental error).

EXAMPLE 23

The reactants, conditions, etc. were the same as those described in Example 22 except that 0.124 g of copper (II) borate was used as the catalyst. A 21.4% yield of propylene diacetate was obtained along with a 2.4% yield of ethylene diacetate and 7.4% yield of methylene diacetate.

EXAMPLE 24

The reactor described in Example 21 was charged with 150 ml of acetic acid, 150 ml of acetic anhydride and 0.078 nickel (II) borate. 2-butene (56 g, 1.0 mol.) was charged and the reactor heated to 140° C. Oxygen was added slowly to a pressure of 200 psig. The reaction was continued for 6 hours and the pressure maintained at 200 psig by addition of oxygen from time to time. The reaction mixture was worked up as in the above examples. NMR analysis indicated a 32.5% yield of diacetate and a 2.5% yield of ethylene diacetate. A small amount of methylene diacetate was also formed. Thus, it may be seen that equal or better yields to the alkylene diacetate relative to the method of U.S. Pat. No. 4,220,800 may be consistently obtained even at the lower temperature of 140° C.

EXAMPLE 25

A 1-liter glass-lined autoclave equipped with a Magnedrive stirrer was charged with 150 ml of acetic acid, 150 ml of acetic anhydride, 0.08g of nickel borate and 56 g of 1-butene. The autoclave was then heated to 140° C. and pressured slowly to about 230 psig with oxygen. The reaction mixture was held at 140° C. for 6 hours. The pressure was maintained at about 230 psig by addition of oxygen from time to time. The reaction mixture was then cooled to room temperature and the 1-butene vented. Most of the solvent (acetic acid/acetic anhydride) was distilled out and the pot residue analyzed by NMR. Butane diol diacetate (9.4 g) and methylene diacetate (1.4 g) were present. Of the products identified, this represents an 87 wt. % selectivity to the butane diacetate.

EXAMPLE 26

The apparatus, quantities, etc. were the same as in Example 25 except that nickel borate was increased to 0.2 g. The sample was distilled to give pure butane diol diacetate in a quantity of 17.8 g with a boiling point of about 65° C. at about 1.2 mm Hg.

Many modifications may be made in the method of this invention by those skilled in the art to maximize the yields of the desirable acetates without departing from the spirit and scope of the invention which is defined only by the appended claims. For example, one skilled in the art could determine an exact combination of transition metal borate catalysts, temperatures, feedstocks and modes of addition to optimize the yield.

We claim:

1. An improved process for the production of alkane hydroxy acetates and diacetates by reacting an olefin or a mixture of olefins with oxygen and acetic anhydride, wherein the improvement comprises conducting the reaction in the presence of a transition metal borate catalyst.

2. The process of claim 1 in which the reaction is conducted at a temperature in the range of 80° to 280° C.

3. The process of claim 2 in which the reaction is conducted at a temperature between 80° and 180° C.

4. The process of claim 1 in which the olefins have 3 to 16 carbon atoms.

5. The process of claim 1 in which the olefin is propylene or 1-butene.

6. The process of claim 1 in which acetic acid is present during the reaction.

7. The process of claim 1 in which the transition metal in the borate catalyst is taken from the group consisting of nickel, copper and iron.

8. The process of claim 1 in which the catalyst is nickel borate.

9. An improved process for the production of alkane hydroxy acetates and diacetates by reacting an olefin or a mixture of olefins with oxygen and acetic anhydride at a temperature in the range of 80° to 280° C., wherein the improvement comprises conducting the reaction in the presence of a transition metal borate catalyst where the transition metal is selected from the group consisting of nickel, copper and iron.

10. The process of claim 9 in which the reaction is conducted at a temperature between 80° and 180° C.

11. The process of claim 9 in which the olefins have 3 to 16 carbon atoms.

12. The process of claim 9 in which the acetic acid is present during the reaction.

13. An improved process for the production of alkane hydroxy acetates and diacetates by reacting an olefin or a mixture of olefins where each molecule has 3 to 16 carbon atoms, with oxygen in the presence of acetic anhydride and acetic acid at a temperature in the range of 80° to 280° C., wherein the improvement comprises conducting the reaction in the presence of a transition metal borate catalyst where the transition metal is selected from the group consisting of nickel, copper and iron.

14. The process of claim 13 in which the reaction is conducted at a temperature between 80° and 180° C.

15. The process of claim 13 in which the olefin is propylene or 1-butene.

16. An improved process for the production of alkane hydroxy acetates and diacetates by reacting an olefin from the group consisting of propylene and 1-butene with oxygen and acetic anhydride at a temperature in the range of 80° to 160° C., wherein the improvement comprises conducting the reaction in the presence of nickel borate.

17. The process in claim 16 in which acetic acid is present with the acetic anhydride.

* * * * *